United States Patent [19]

Gueremy et al.

[11] Patent Number: 5,008,280
[45] Date of Patent: Apr. 16, 1991

[54] 2-IMINOBENZOTHIAZOLINE DERIVATIVES, THEIR PREPARATION AND PHARMACEUTICAL COMPOSITIONS CONTAINING THEM

[75] Inventors: Claude Gueremy, Houilles; Patrick Jimonet, Villepreux; Serge Mignani, Livry Gargan, all of France

[73] Assignee: Rhone-Poulenc Sante, Antony, France

[21] Appl. No.: 450,231

[22] Filed: Dec. 13, 1989

[30] Foreign Application Priority Data

Dec. 15, 1988 [FR] France .............................. 88 16546
Jul. 13, 1989 [FR] France .............................. 89 09480

[51] Int. Cl.$^5$ ................. C07D 277/82; A61K 31/425
[52] U.S. Cl. .................................... 514/367; 514/321; 546/198; 548/156; 548/161
[58] Field of Search ................ 548/164, 156; 514/367, 514/321; 546/198

[56] References Cited

U.S. PATENT DOCUMENTS 4,918,090 4/1990 Johnson ............................... 548/164

Primary Examiner—Robert Gerstl
Attorney, Agent, or Firm—Morgan & Finnegan

[57] ABSTRACT

Compounds of the formula:

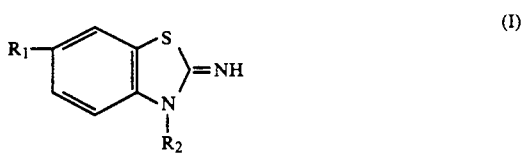

(I)

in which - $R_1$ denotes a polyfluoroalkoxy or polyfluoroalkyl radical, and - $R_2$ denotes either a chain —$CH_2$—$(CH(R_4))_n$—$R_3$, in which $R_3$ denotes a dialkylamino, piperidino, 1-pyrrolidinyl, mercapto, acylthio, alkylthio, alkylsulphinyl or alkylsulphonyl radical, $R_4$ denotes a hydrogen atom or an alkyl radical and n is equal to 0 or 1, or a residue of formula:

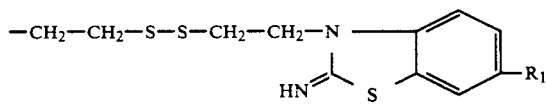

the said alkyl and alkoxy radicals and portions containing 1 to 4 carbon atoms each in a straight or branched chain and said the acyl portions containing 2 to 4 carbon atoms each, and the salts of these compounds, are useful in the treatment of diseases in which glutamate is implicated.

6 Claims, No Drawings

2-IMINOBENZOTHIAZOLINE DERIVATIVES, THEIR PREPARATION AND PHARMACEUTICAL COMPOSITIONS CONTAINING THEM

DETAILED DESCRIPTION OF THE INVENTION

The present invention provides, as new compounds, the 2-iminobenzothiazoline derivatives of formula:

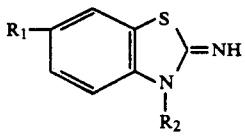
(I)

and their salts, in which $R_1$ represents a polyfluoroalkoxy or polyfluoroalkyl radical, and $R_2$ represents
either a residue of formula $-CH_2-(CH(R_4))_n-R_3$, in which $R_3$ represents dialkylamino, piperidino, 1-pyrrolidinyl, mercapto, acylthio, alkylthio, alkylsulphinyl or alkylsulphonyl, $R_4$ represents a hydrogen atom or an alkyl radical and n is 0 or 1, or a residue of formula:

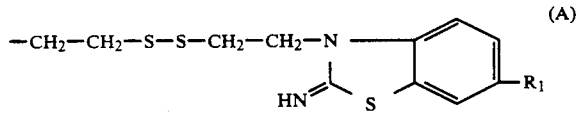
(A)

Except where otherwise stated, in the definitions above and those mentioned below, the alkyl radicals and alkyl and alkoxy portions contain 1 to 4 carbon atoms each in a straight or branched chain and the acyl portions contain 2 to 4 carbon atoms each.

The polyfluoroalkoxy radical is preferably trifluoromethoxy, pentafluoroethoxy, 2,2,2-trifluoroethoxy or 1,1,2,2-tetrafluoroethoxy.

The addition salts of the compounds of formula (I) with inorganic or organic acids and the enantiomers of the compounds of formula (I) containing an asymmetric center are part of the invention.

According to a feature of the invention, the compounds of formula (I), with the exception of those for which $R_2$ denotes a residue of formula (A) or $R_3$ denotes an acylthio radical, are prepared by the reaction of an amino derivative of formula:

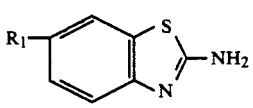
(II)

in which $R_1$ has the same meanings as in the formula (I), with a derivative of formula:

$R_2-X$ (III)

in which $R_2$ has the same meanings as in the formula (I) and X denotes a reactive group such as a tosyloxy radical or a halogen (preferably chlorine, bromine or iodine) atom, or an addition salt of such a compound with an inorganic or organic acid.

This reaction is generally performed in an inert organic solvent such as an alcohol (e.g. ethanol or propanol), a ketone (e.g. acetone or methyl ethyl ketone) or dimethylformamide, at a temperature between 10° C. and the boiling point of the solvent, optionally in the presence of sodium iodide and optionally after melting the mixture of the compounds of formulae (II) and (III) at 130°–140° C.

The compounds of formula (II) may be obtained by application or adaptation of the method described by L. M. YAGUPOL'SKII et al., Zh. Obshch. Khim., 33(7), 2301-7, 1963 (Chem. Abst., vol. 60, 692 a–f, 1964) or the method described in U.S. Pat. No. 2,822,359.

The compounds of formula (III) are commercially available or may be prepared by application or adaptation of the method described by T. P. DAWSON, J. Amer. Chem. Soc., 69, 1211 (1947) or the methods described in the examples.

According to a further feature of the invention, the compounds of formula (I) in which $R_2$ denotes a residue of formula: $-CH_2-(CH(R_4))_n-R_3$ in which $R_3$ represents alkylsulphinyl or alkylsulphonyl and $R_4$ and n are defined as above may also be obtained by oxidation of the corresponding derivatives in which $R_3$ represents alkylthio.

The oxidation to alkylsulphinyl is generally accomplished with m-chloroperbenzoic acid, in an alcohol such as methanol or ethanol, at a temperature in the region of $-20°$ C.

The oxidation to alkylsulphonyl is generally accomplished with hydrogen peroxide, in acetic acid, at a temperature in the region of 100.C, or by means of m-chloroperbenzoic acid, in a chlorinated solvent such as methylene chloride or chloroform, at a temperature in the region of 20° C.

According to another feature of the invention, the compounds of formula (I) in which $R_2$ denotes a residue of formula: $-CH_2-(CH(R_4))_n-R_3$ in which $R_3$ denotes mercapto and $R_4$ and n are defined as above may also be prepared by hydrolysis of a corresponding derivative in which $R_3$ denotes tert-butylthio.

This hydrolysis is generally accomplished with hydrobromic acid, at a temperature in the region of 110° C.

The compounds of formula (I) in which $R_2$ represents a residue of formula: $-CH_2-(CH(R_4))_n-R_3$ in which $R_3$ represents acylthio, may be obtained by hydrolysis of a derivative of formula:

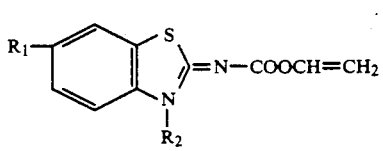
(IV)

in which $R_1$ has the same meanings as in the formula (I) and $R_2$ has the same meaning as above.

This reaction is generally accomplished using hydrobromic acid in acetic acid, at a temperature in the region of 20° C.

The derivatives of formula (IV) may be obtained by the action of a derivative of formula:

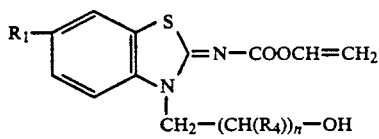

in which $R_1$, $R_4$ and n have the same meanings as in formula (I), on thiolacetic acid.

This reaction is performed in the presence of triphenylphosphine and ethyl azodicarboxylate, in an inert solvent such as tetrahydrofuran, at a temperature of between 0° and 20° C.

The derivatives of formula (V) may be prepared by the action of a derivative of formula:

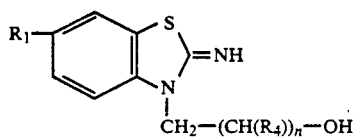

in which $R_1$ has the same meanings as in the formula (I), on vinyloxycarbonyl chloride.

This reaction is generally performed in an inert solvent such as dichloromethane, in the presence of a tertiary amine.

The derivatives of formula (VI) may be obtained by the action of a derivative of formula (II) on a derivative of formula (III) in which $R_2$ denotes a residue of formula: $-CH_2-(CH(R_4))_n-OH$.

This reaction is performed under the conditions stated above for the reaction of the derivatives of formulae (II) and (III).

The compounds of formula (I) in which $R_2$ denotes a residue of formula (A) may be prepared by the action of hydrobromic acid on a 3-(2-tert-butylthioethyl)-2-imino-6-polyfluoroalkoxy- or -polyfluoroalkylbenzothiazoline. Preferably, this reaction is performed at a temperature in the region of 120° C.

The reaction mixtures obtained by the various processes described above are treated according to conventional physical methods (evaporation, extraction, distillation, crystallization, chromatography, etc.) or chemical methods (salt formation, etc.).

The enantiomers of the compounds of formula (I) containing an asymmetric center may be obtained by resolution of the racemates, e.g. by chromatography on a chiral column according to the method of W. H. PIRKLE et al., Asymmetric synthesis, vol. 1, Academic Press (1983) or alternatively by synthesis from chiral precursors.

The compounds of formula (I), in free base form, can be optionally converted into addition salts with an inorganic or organic acid, by the action of such an acid in an organic solvent such as an alcohol, ketone, ether or chlorinated solvent.

The compounds of formula (I) and their salts possess advantageous pharmacological properties. They are useful in the treatment of medical conditions associated with the efforts of glutamate in which it is desirable to inhibit such effects at least partially. Thus the new compounds are active in the treatment of glutamate-induced convulsions, and are useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebellar atrophy.

The activity of the compounds of formula (I) with respect to glutamate-induced convulsions was determined by a technique based on that of I. P. LAPIN, J. Neural. Transmission, vol. 54, 229–238 (1982); intracerebroventricular injection of glutamate was performed according to a technique based on that of R. CHERMAT and P. SIMON, J. Pharmacol. (Paris), vol. 6, 489–492 (1975). The $ED_{50}$ of the compounds of the invention does not exceed 3 mg/kg when administered i.p. (intraperitoneally).

The compounds of formula (I) possess low toxicity. Their $LD_{50}$ is above 15 mg/kg when administered i.p. in mice.

The following compounds are especially advantageous:

3-(N,N-dimethylaminoethyl)-2-imino-6-trifluoromethoxybenzothiazoline, 2-imino-3-(2-piperidinoethyl)-6-trifluoromethoxybenzothiazoline, 3-[2-(1-pyrrolidinyl)ethyl]-2-imino-6-trifluoromethoxybenzothiazoline, 2-imino-3-(2-methylthioethyl)-6-trifluoromethoxybenzothiazoline, 3-(2-ethylthioethyl)-2-imino-6-trifluoromethoxybenzothiazoline, 3-(2-ethylsulphinylethyl)-2-imino-6-trifluoromethoxybenzothiazoline, 3-(2-ethylsulphonylethyl)-2-imino-6-trifluoromethoxybenzothiazoline, 2-(2-imino-6-trifluoromethoxy-3-benzothiazolinyl)ethanethiol, 2-imino-3-(2-methylsulphinylethyl)-6-trifluoromethoxybenzothiazoline, 3-(2-ethylthioethyl)-2-imino-6-trifluoromethylbenzothiazoline, 2-imino-3-methylthiomethyl-6-trifluoromethoxybenzothiazoline, 2-imino-3-methylsulphinylmethyl-6-trifluoromethoxybenzothiazoline, 2-imino-3-(2-propylthioethyl)-6-trifluoromethoxybenzothiazoline, 2-imino-3-(2-methylsulphonylethyl)-6-trifluoromethoxybenzothiazoline, and 2-imino-3-(2-ethylsulphinylethyl)-6-trifluoromethylbenzothiazoline.

For medicinal use, the compounds of formula (I) may be employed as they are, or in the form of pharmaceutically acceptable salts, i.e. salts which are non-toxic at the doses at which they are used.

As examples of pharmaceutically acceptable salts, the addition salts with inorganic or organic acids, such as acetate, propionate, succinate, benzoate, fumarate, maleate, oxalate, methanesulphonate, isethionate, theophyllineacetate, salicylate, phenolphthalinate, methylenebis-($\beta$-hydroxynaphthoate), hydrochloride, sulphate, nitrate and phosphate, may be mentioned.

EXAMPLES

The examples which follow illustrate the invention.

EXAMPLE 1

2-Amino-6-trifluoromethoxybenzothiazole (7 g) and 2-chloro-N,N-dimethylethylamine (4.8 g) are heated for 1 hour to 130° C. 2-Propanol (10 cc) is added and heating is continued for 20 hours to boiling. After cooling to a temperature in the region of 20° C., the reaction medium is concentrated at 40° C. under reduced pressure (20 mm Hg; 2.7 kPa) and the residue treated with 1N sodium hydroxide (40 cc). After extraction with dichloromethane (100 cc), drying over magnesium sulphate and concentration at 40° C. under reduced pressure, the residue is purified by chromatography on a silica column with a mixture of ethyl acetate and methanol (90:10 by volume) as eluent. 3-(2-Dimethyl-aminoethyl)-2-imino-6-trifluoromethoxybenzothiazoline (2.1 g) is obtained in the form of a yellowish oil, which is converted to a dihydrochloride subliming at about 200° C.

2-Amino-6-trifluoromethoxybenzothiazole may be prepared according to the method described by L. M. YAGUPOL'SKII et al., Zh. Obshch. Khim., 33 (7), 2301 (1963).

EXAMPLE 2

2-Amino-6-trifluoromethoxybenzothiazole (9.4 g) and N-(2-chloroethyl)piperidine hydrochloride (8.1 g) are heated for 1 hour to 130° C. Dimethylformamide (20 cc) is then added and the reaction is continued for 24 hours at 130° C. After cooling of the mixture to a temperature in the region of 20° C., the precipitate is filtered off and then treated with 1N sodium hydroxide (50 cc) in distilled water (100 cc). The residue obtained by extraction with dichloromethane, drying over magnesium sulphate and concentration to dryness under reduced pressure (20 mm Hg; 2.7 kPa) is purified by chromatography on a silica column, with ethyl acetate and then a mixture of ethyl acetate and methanol (95:5 by volume) as eluents. 2-Imino-3-(2-piperidinoethyl)-6-trifluoromethoxybenzothiazoline (2.9 g) is obtained in the form of a yellow oil, which is converted to a dihydrochloride subliming at about 200° C. after recrystallization in boiling absolute ethanol (20 cc).

( EXAMPLE 3

2-Amino-6-trifluoromethoxybenzothiazole (9.4 g) and N-(2-chloroethyl)pyrrolidine hydrochloride (7.5 g) are heated for 2 hours to 130° C. 2-Propanol (30 cc) is then added and the reaction is continued for 40 hours at the boiling point. After cooling of the mixture to a temperature in the region of 20° C., the precipitate is filtered off and then treated with 1N sodium hydroxide (20 cc) in distilled water (100 cc). The residue obtained by extraction with dichloromethane, drying over magnesium sulphate and concentration to dryness under reduced pressure (20 mm Hg; 2.7 kPa) is taken up in ethyl ether (50 cc) and treated with 4.2N ethereal hydrogen chloride (3.1 cc). After recrystallization in boiling 2-propanol (50 cc), 3-[2-(1-pyrrolidinyl)ethyl]-2-imino-6-trifluoromethoxybenzothiazoline (1.9 g), m.p. above 260° C., is obtained.

EXAMPLE 4

A mixture of 2-amino-6-trifluoromethoxybenzothiazole (40 g) and 1-chloro-2-methylthioethane (22.2 g) in methyl ethyl ketone (250 cc) is heated for 18 hours to boiling and then cooled to a temperature in the region of 20° C. The precipitate formed is filtered off and the filtrate concentrated at 40° C. under reduced pressure (20 mm Hg; 2.7 kPa) to a volume of approximately 100 cc. The reaction is thereafter continued for 72 hours at the boiling point and then, after cooling of the mixture to a temperature in the region of 20° C., the further precipitate formed is filtered off and combined with that formed previously. After washing of the product with ethyl ether (200 cc), 2-imino-3-(2-methylthioethyl)-6-trifluoromethoxybenzo-thiazoline hydrochloride (31.9 g), m.p. 218° C., is obtained.

EXAMPLE 5

A mixture of 2-amino-6-trifluoromethoxybenzothiazole (9.4 g) and 1-chloro-2-ethylthioethane (5.5 g) in methyl ethyl ketone (20 cc) is heated for 15 hours to boiling. The precipitate formed is filtered off while hot and washed with boiling methyl ethyl ketone (2×20 cc). 3-(2-Ethylthioethyl)-2-imino-6-trifluoro-methoxybenzothiazoline hydrochloride (11.5 g), subliming at about 160° C., is obtained.

EXAMPLE 6

3-(2-tert-Butylthioethyl)-2-imino-6-trifluoromethoxybenzothiazoline hydrochloride (1.5 g) and 47% strength hydrobromic acid (15 cc) are heated for 4 hours to 100° C. After cooling of the mixture to 0° C., the precipitate formed is filtered off and washed with distilled water (2×25 cc) and then with ethyl ether (2×30 cc). 2-(2-Imino-6-trifluoromethoxy-3-benzothiazolinyl)ethanethiol hydrobromide (0.9 g), m.p. 180° C., is obtained.

3 (2-tert-Butylthioethyl)-2-imino-6-trifluoromethoxybenzothiazoline hydrochloride may be prepared according to the following process: 2-amino-6-trifluoromethoxybenzothiazole (9.4 g) and 2-chloro-1-tert-butylthioethane (6.7 g) in methyl ethyl ketone (30 cc) are heated for 42 hours to boiling. After cooling of the reaction medium to 0° C., the precipitate formed is filtered off and washed with methyl ethyl ketone (2×20 cc). 3-(2-tert-Butylthioethyl)-2-imino-6-trifluoromethoxybenzothiazoline hydrochloride (3.7 g), melting to form a resin at about 180°-190° C., is obtained.

2-Chloro-1-tert-butylthioethane may be prepared according to the method described by T. P. DAWSON, J. Am. Chem. Soc., 69, 1211 (1947).

EXAMPLE 7

3-(2-Ethylthioethyl)-2-imino-6-trifluoromethoxybenzothiazoline (5 g), 30% strength hydrogen peroxide (10 cc) and acetic acid (70 cc) are heated for 24 hours to 100° C. After cooling to a temperature in the region of 20° C., the reaction mixture is added to distilled water (200 cc) cooled to 0° C., treated with 30% strength sodium hydroxide (120 cc) and then extracted with ethyl acetate (300 cc). The organic phase is washed with distilled water (150 cc) and then with aqueous sodium bifsulphite solution (2×150 cc), dried over magnesium sulphate and concentrated to dryness under reduced pressure (20 mm Hg; 2.7 kPa). After formation of the hydrochloride by adding 1N hydrochloric acid (16 cc) in chloroform (25 cc), 3-(2-ethylsulphonylethyl)-2-imino-6-trifluoromethoxybenzothiazoline hydrochloride (1.9 g), m.p. 212° C., is obtained.

EXAMPLE 8 m-Chloroperbenzoic acid (0.9 g) is added in the course of approximately 10 minutes to 3-(2-ethylthioethyl)-2-imino-6-trifluromethoxybenzothiazoline (1.7 g) in absolute ethanol (25 cc) cooled to −20° C. The reaction is continued for 30 minutes at the same temperature. The precipitate formed is filtered off, then taken up in ethyl ether (50 cc) and treated with 4N ethereal hydrogen chloride (2 cc). After filtration, (RS)-3-(2- ethylsulphinylethyl)-2-imino-6-trifluoro-methoxybenzothiazoline hydrochloride (1.1 g), m.p 174° C., is obtained.

EXAMPLE 9

The procedure is as in Example 8, starting with 2-imino-3-(2-methylthioethyl)-6-trifluoromethoxybenzothiazoline (3.7 g) and m-chloroperbenzoic acid (2.3 g) in absolute ethanol (60 cc). After 30 minutes at −20° C., the precipitate formed is filtered off and the hydro-chloride prepared in acetone (60 cc). (RS)-2-Imino-3-(2-methylsulphinylethyl)-6-trifluoromethoxybenzo-thiazoline hydrochloride (1.5 g), m.p. 186° C., is obtained.

EXAMPLE 10

2-Amino-6-trifluoromethylbenzothiazole (6.55 g) and 1-chloro-2-ethylthioethane (7.48 g) in methyl ethyl ketone (20 cc) are heated for 18 hours to boiling and the mixture is then cooled to a temperature in the region of 20° C. After concentration to dryness at 50° C. under reduced pressure (20 mm Hg; 2.7 kPa), the residue is taken up in methyl ethyl ketone (50 cc). The precipitate formed is filtered off and recrystallized in 2-propanol (50 cc). 3-(2-Ethylthioethyl)-2-imino-6-trifluoromethylbenzothiazoline hydrochloride (3.1 g), subliming at about 160° C., is obtained.

2-Amino-6-trifluoromethylbenzothiazole may be prepared according to the method described in U.S. Pat. No. 2,822,359.

EXAMPLE 11

3-(2-tert-Butylthioethyl)-2-imino-6-trifluoromethoxybenzothiazoline hydrochloride (16.8 g) and 48% strength hydrobromic acid (500 cc) are heated to 120° C. for 18 hours. The precipitate formed is filtered off and washed with distilled water (2×50 cc) and then with ethyl ether (2×50 cc). Bis[2-(2-imino-6-trifluoromethoxy-3-benzothiazolinyl)ethyl]disulphide dihydrobromide (10.0 g), m.p. above 260° C., is obtained.

EXAMPLE 12

A mixture of 2-amino-6-trifluoromethoxybenzothiazole (16.4 g) and chloromethyl methyl sulphide (8.1 g) in methyl ethyl ketone (30 cc) is stirred for 9 hours at a temperature in the region of 20° C. The precipitate formed is filtered off and recrystallized twice in absolute ethanol. 2-Imino-3-methylthiomethyl-6-trifluoromethoxybenzothiazoline hydrochloride (5.5 g), subliming at about 170° C., is obtained.

EXAMPLE 13

2-Imino-3-methylthiomethyl-6-trifluoromethoxybenzothiazoline hydrochloride (3.35 g) is added to m-chloroperbenzoic acid (7.6 g) dissolved in dichloromethane (70 cc) cooled to 0° C. The reaction is continued for 2 hours at 10°-15° C. The precipitate formed is filtered off and treated with aqueous sodium hydroxide to neutrality, and the organic phase extracted with ethyl acetate. After purification by chromatography on a silica column with a mixture of ethyl acetate and methanol (90:10 by volume) as eluent, (RS)-2-imino-3-methylsulphinylmethyl-6-trifluoromethoxybenzothiazoline (1.0 g), converted to the form of a hydrochloride subliming at 150°-155° C., is obtained.

EXAMPLE 14

A mixture of 2-amino-6-trifluoromethoxybenzothiazole (9.4 g) and 1-chloro-2-propylthioethane (6.1 g) in methyl ethyl ketone (30 cc) is heated for 72 hours to boiling. The precipitate formed is filtered off, washed with methyl ethyl ketone (2×20 cc) and recrystallized in 2-propanol (30 cc). 2-Imino-3-(2-propylthioethyl)-6-trifluoromethoxybenzothiazoline hydrochloride (5.8 g), m.p. 187° C., is obtained.

EXAMPLE 15 m-Chloroperbenzoic acid (2.1 g) is added in the course of approximately 5 minutes to (RS)-2-imino-3-(2-methylsulphinylethyl)-6-trifluoromethoxybenzothiazoline (3.4 g) in dichloromethane (70 cc) cooled to 0° C. The reaction is continued for 30 minutes at the same temperature. The precipitate formed is filtered off, then taken up in a mixture of dichloromethane (100 cc) and absolute ethanol (15 cc) and treated with 4N ethereal hydrogen chloride (6 cc). After filtration and recrystallization in a mixture of 2-propanol (50 cc) and distilled water (15 cc), 2-imino-3-(2-methylsulphonylethyl)-6-trifluoromethoxybenzothiazoline hydrochloride (2.3 g), subliming at about 210° C., is obtained.

(EXAMPLE 16 m-Chloroperbenzoic acid (6.6 g) is added gradually to 3-(2-ethylthioethyl)-2-imino-6-trifluoromethylbenzothiazoline hydrochloride (3.0 g) suspended in dichloromethane (75 cc) cooled to 0° C. The reaction is continued for 2 hours at a temperature in the region of 20° C. The precipitate formed is filtered off and then recrystallized in 2-propanol (20 cc). 3-(2-Ethyl-sulphonylethyl)-2-imino-6-trifluoromethylbenzo-thiazoline hydrochloride (0.8 g), subliming at about 180° C., is obtained.

EXAMPLE 17

70-75% pure m-chloroperbenzoic acid (4.3 g) is added in the course of approximately 10 minutes to 2-imino-3-(2-propylthioethyl)-6-trifluoromethoxybenzothiazoline (5.87 g) dissolved in absolute ethanol (80 cc) cooled to −35° C. The reaction is continued for 10 minutes at the same temperature. The reaction medium is then added to ethyl ether (300 cc) and treated with 4.2N ethereal hydrogen chloride (4.2 cc). The precipitate formed is filtered off, then taken up in distilled water (50 cc) and neutralized with 1N sodium hydroxide. After extraction with ethyl acetate, drying over magnesium sulphate and concentration to dryness under reduced pressure (20 mm Hg; 2.7 kPa), the crude product is purified by chromatography on a silica column, with ethyl acetate and then a mixture of ethyl acetate and methanol (90:10 by volume) as eluents. After conversion to hydrochlorides, 2-imino-3-(2-propylsulphonylethyl)-6-trifluoromethoxybenzothiazoline hydrochloride (0.33 g), subliming at about 200° C., and (RS)-2-imino-3-(2-propylsulphinylethyl)-6-trifluoromethoxybenzothiazoline hydrochloride (2.63 g), m.p. 125° C., are obtained.

EXAMPLE 18

2-Amino-6-trifluoromethoxybenzothiazole (14.2 g) and 2-bromo-1-methylthiopropane (13.2 g) in methyl ethyl ketone (30 cc) are heated for 3 hours to boiling. The precipitate formed is filtered off, washed with methyl ethyl ketone (2×50 cc) and recrystallized in 2-propanol (50 cc). (RS)-2-Imino-3-(2-methylthiopropyl)-6-trifluoromethoxybenzothiazoline hydrobromide (11.5 g), subliming at about 180° C., is obtained.

2-Bromo-1-methylthiopropane may be prepared according to the following method: phosphorus tribromide (9 ml) is added dropwise to 1-methylthio-2-propanol (27.6 g) cooled to 0° C. The reaction is continued for 4 hours at the same temperature and the reaction medium is then hydrolysed by adding distilled water (50 cc) slowly. Extraction with ethyl ether leads, after drying, filtration and concentration to dryness under reduced pressure (20 mm Hg; 2.7 kPa), to 2-bromo-1-methylthiopropane (13.2 g) in the form of yellow oil.

1-Methylthio-2-propanol may be prepared in the following manner: 1-Chloro-2-propanol (21.3 cc) is added dropwise to sodium methanethiolate (17.6 g) stirred at a temperature in the region of 20° C. in absolute ethanol (100 cc). The reaction medium is then heated to boiling for 3 hours. After concentration to dryness under reduced pressure, the residue is extracted with ethyl acetate (300 cc) and the organic phase washed with distilled water and then dried, filtered and concentrated to dryness under reduced pressure. 1-Methylthio-2-propanol (19.8 g) is obtained in the form of a yellow oil.

EXAMPLE 19

70% pure m-chloroperbenzoic acid (4.74 g) is added in the course of approximately 10 minutes to (RS)-2-imino-3-(2-methylthiopropyl)-6-trifluoromethoxybenzo-thiazoline (6.2 g) in absolute ethanol (80 cc) cooled to −40° C. The reaction is continued for 10 minutes at the same temperature. The reaction medium is added to ethyl ether (200 cc) and treated with 4.2N ethereal hydrogen chloride (5 cc). The precipitate formed is filtered off, then taken up in distilled water (50 cc) and treated with aqueous sodium hydroxide to neutrality. Extraction with ethyl acetate leads, after the usual treatment, to a crude product (6.7 g), purified by chromatography on a silica column with a mixture of ethyl acetate and methanol (95:5 by volume) as eluent. 2-Imino-3-(2-methylsulphonylpropyl)-6-trifluoromethoxybenzothiazoline (0.8 g), the hydrochloride of which sublimes at about 200° C., 2-imino-3-(2-methylsulphinylpropyl)-6-trifluoromethoxybenzothiazoline (isomer A) (1.3 g), the hydrochloride of which sublimes at about 200° C., and 2-imino-3-(2-methylsulphinylpropyl)-6-trifluoromethoxybenzothiazoline (isomer B) (0.8 g), the hydrochloride of which melts at 134° C., are obtained.

EXAMPLE 20

3-(2-Acetylthioethyl)-2-vinyloxycarbonylimino-6-trifluoromethoxybenzothiazoline (3.0 g) in acetic acid (30 cc) are stirred for 18 hours at a temperature in the region of 20° C. in the presence of 47% strength hydrobromic acid (3 cc). After the addition of distilled water (100 cc) and neutralization using 30% strength sodium hydroxide, extraction with ethyl acetate followed by the usual treatment leads to an oil (1.2 g) which crystallizes. Formation of the hydrochloride in a mixture of ethyl ether and ethyl acetate by treatment with ethereal hydrogen chloride is followed by recrystallization in ethyl acetate, leading to 3-(2-acetylthioethyl)-2-imino-6-trifluoromethoxy-benzothiazoline hydrochloride (0.5 g), subliming at about 160° C.

3-(2-Acetylthioethyl)-2-vinyloxycarbonylimino-6-trifluoromethoxybenzothiazoline may be obtained in the following manner: ethyl azodicarboxylate (10.5 cc) is added dropwise to triphenylphosphine (17.6 g) dissolved in tetrahydrofuran (150 cc) at 0° C. Stirring is continued for 30 minutes at this temperature. A solution of thiolacetic acid (4.8 cc) and 3-(2-hydroxyethyl)-2-vinyloxycarbonylimino-6-trifluoromethoxybenzothiazoline (11.7 g) in tetrahydrofuran (75 cc) is then added gradually. The reaction is continued for 1 hour at 0° C. and then 1 hour at a temperature in the region of 20° C. After concentration to dryness under reduced pressure (20 mm Hg; 2.7 kPa), the residue obtained is taken up in methanol (50 cc), then filtered and washed once with methanol (50 cc). 3-(2-Acetylthioethyl)-2-vinyloxycarbonylimino-6-trifluoromethoxybenzothiazoline (10.4 g), m.p. 173° C., is obtained.

3-(2-Hydroxyethyl)-2-vinyloxycarbonylimino-6-trifluoromethoxybenzothiazoline may be prepared in the following manner: vinyloxycarbonyl chloride (4.8 cc) is added dropwise at 0° C. to 3-(2-hydroxyethyl)-2-imino-6-trifluoromethoxybenzothiazoline (20 g) dissolved in dichloromethane (200 cc) in the presence of triethylamine (7.9 cc). Stirring is continued for 2 hours at a temperature in the region of 20° C. The precipitate formed is filtered off, washed with water and dried. 3-(2-Hydroxyethyl)-2-vinyloxycarbonylimino-6-trifluoromethoxybenzothiazoline (11.7 g), m.p. 190° C., is obtained.

3-(2-Hydroxyethyl)-2-imino-6-trifluoromethoxybenzothiazoline may be prepared in the following manner: 2-amino-6-trifluoromethoxybenzothiazole (9.4 g) and 2-bromoethanol (10 g) in absolute ethanol (30 cc) are heated for 95 hours to boiling. The mixture is cooled to a temperature in the region of 20° C. The precipitate formed is filtered off and washed with ethyl ether (100 cc). 3-(2-Hydroxyethyl)-2-imino-6-trifluoromethoxybenzothiazoline hydrobromide (6.4 g), m.p. 219° C., is thereby obtained.

EXAMPLE 21

A solution, dried over magnesium sulphate and prepared from 50% pure m-chloroperbenzoic acid (0.75 g) and dichloromethane (5 cc), is added in the course of 15 minutes with stirring to a solution, cooled to −5° C., of 3-(2-ethylthioethyl)-2-imino-6-pentafluoroethoxy-benzothiazoline (0.4 g) in dichloromethane (6 cc). The mixture is left stirring for one hour while the temperature is maintained at between −5° C. and 0° C., and the benzoic acid formed is then removed by filtration; the filtrate is thereafter diluted with ethyl ether (50 cc) and acidified with a 5N ethereal hydrochloric acid solution. 3-(2-Ethylsulphonylethyl)-2-imino-6-pentafluoroethoxybenzothiazoline hydrochloride (0.25 g), m.p. 230° C., is thereby obtained.

3-(2-Ethylthioethyl)-2-imino-6-pentafluoroethoxybenzothiazoline may be prepared in the following manner: a mixture of 6-pentafluoroethoxy-2-benzothiazolamine (0.5 g), methyl ethyl ketone (15 cc) and 2-chloroethyl ethyl sulphide (0.45 cc) is heated on an oil bath to 110° C. for 25 hours. The methyl ethyl ketone is evaporated off at 45° C. under reduced pressure (20 mm Hg; 2.7 kPa) and the evaporation residue is taken up with water (30 cc), alkalinized with 28% strength ammonia solution and extracted three times with ethyl ether (60 cc in total). After evaporation under vacuum (20 mm Hg; 2.7 kPa), the dark red residue (0.7 g) is purified by chromatography on a silica column, eluting with a mixture of cyclohexane and ethyl acetate (70:30 by volume). 3-(2-Ethylthioethyl)-2-imino-6-pentafluoroethoxybenzothiazoline (0.42 g) is thereby obtained in the form of an oil, which crystallizes, m.p. below 50° C.

6-Pentafluoroethoxy-2-benzothiazolamine may be prepared in the following manner: potassium thiocyanate (8.15 g) is added, while the apparatus is flushed with argon, to a solution of 4-pentafluoro-ethoxyaniline (4.8 g) in acetic acid (35 cc), and the mixture is stirred for 10 minutes at a temperature in the region of 20° C. To the solution thereby obtained, a solution of bromine (1.1 cc) in acetic acid (10 cc) is introduced dropwise in the course of 35 minutes at a temperature of between 22° and 42° C.; the mixture is then stirred for 20 hours at a temperature in the region of 20° C. The reaction mixture is poured into a mixture of water and ice (250 cc), alkalinized with 28% strength ammonia solution (50 cc) and extracted twice with ethyl acetate (250 cc in total). After settling has taken place, the organic solution is washed with distilled water to pH 8, dried over magnesium sulphate, filtered and evaporated at 50° C. under reduced pressure (20 mm Hg; 2.7 kPa). The product obtained (6.3 g) is purified by chromatography on a column of silica (650 g; particle size: 0.063–0.200 mm) with a mixture of cyclohexane and ethyl acetate (50:50 by volume) as eluent, and recrystallized in boiling cyclohexane (400 cc). 6-Pentafluoroethoxy-2-benzothiazolamine (3.25 g), m.p. 156° C., is obtained.

4-Pentafluoroethoxyaniline may be prepared according to the method described by W. A. SHEPPARD, J. Org. Chem., 29, 1 (1964).

EXAMPLE 22

The procedure is as in Example 21, starting with 3-(2-ethylthioethyl)-2-imino-6-pentafluoroethylbenzothiazoline (6.6 g), 80% pure meta-chloroperbenzoic acid (12 g) and dichloromethane (200 cc). After chromatography on a silica column with ethyl acetate as eluent, a pink solid (2.6 g) is recovered, which solid is recrystallized twice in a mixture of cyclohexane and ethyl acetate (80:20 by volume). 3-(2-Ethylsulphonylethyl)-2-imino-6-pentafluoroethylbenzothiazoline (1 g), m.p. 125° C., is thereby obtained.

3-(2-Ethylthioethyl)-2-imino-6-pentafluoroethylbenzothiazoline may be prepared in the following manner: a mixture of 6-pentafluoroethyl-2-benzo-thiazolamine (11.2 g), 2-chloroethyl ethyl sulphide (6 cc) and methyl ethyl ketone (20 cc) is heated to reflux for 18 hours. The solvent is then evaporated off under reduced pressure (20 mm Hg; 2.7 kPa) and the evaporation residue is taken up with water (200 cc), alkalinized with 28% strength ammonia solution and extracted with ethyl acetate (500 cc in total). After evaporation under vacuum (20 mm Hg; 2.7 kPa), the orange-colored residue is purified by chromatography on a silica column, eluting with a mixture of cyclohexane and ethyl acetate (60:40 by volume). 3-(2-Ethylthioethyl)-2-imino-6-pentafluoroethylbenzothiazoline (7.5 g) is thereby obtained in the form of an oil, which crystallizes, m.p. below 50° C.

6-Pentafluoroethyl-2-benzothiazolamine may be prepared using the procedure in Example 21 for the preparation of 6-pentafluorethoxy-2-benzothiazolamine, but starting with 4-pentafluoroethylaniline (14.6 g), potassium thiocyanate (14 g) and bromine (3.6 cc) in acetic acid (150 cc). After purification on a silica column with a mixture of cyclohexane and ethyl acetate (50:50 by volume) as eluent, 6-pentafluoroethyl-2-benzothiazolamine (17 g), m.p. about 100° C., is obtained.

4-Pentafluoroethylaniline may be prepared according to the method described in German Patent No. 2,606,982.

EXAMPLE 23

A solution, dried over magnesium sulphate and prepared from 50% pure m-chloroperbenzoic acid (38g) and dichloromethane (300 cc) is added drop by drop with stirring to a solution, cooled to −5° C., of 3-(2-ethylthioethyl)-2-imino-6-trifluoromethylbenzothiazoline (30.8 g) in dichloromethane (300 cc). The mixture is allowed to return to 20° C. and water (100 cm$^3$) is added to the reaction mixture which is then made alkaline to pH 10 with 28% ammonia. A white precipitate appears which is separated by filtration. The filtrate is separated and the organic phase is dried over magnesium sulphate and evaporated under reduced pressure (20 mmHg 2.7 kPa). The evaporation residue is chromatographed on a column of silica, eluting with a mixture of ethyl acetate and ethanol (80:20 by volume). A cream colored solid (26 g) is thus obtained which is converted into the hydrochloride in ethyl ether. After 3 recrystallisations from ethanol, (RS)-2-imino-3-(2-ethylsulphinylethyl)-6-trifluoromethylbenzothiazoline hydrochloride (2.9 g), m.p. 150° C., is obtained.

2-Imino-3(2-ethylthioethyl)-6-trifluoromethylbenzothiazoline can be obtained in the following manner: A mixture of 6-trifluoromethyl-2-benzothiazolamine (32.3 g), 2-chloroethylsulphide (18 cc) and methylethylketone (20 cc) is heated under reflux for 16 hours. After cooling to 20° C., acetone (20 cc) is added and the solution obtained is poured into a mixture of ethyl acetate (200 cc) and petroleum ether (40°-60° C., 200 cc). The precipitate obtained is filtered off, taken up in water, and made alkaline with 28% ammonia. The base is then extracted with a mixture of ethylacetate (150 cc) and cyclohexane (150 cc) and purified on a column of silica (600 g), eluting with a mixture of ethylacetate and cyclohexane (50:50 by volume). 2-Imino-3-(2-ethylthioethyl)-6-trifluoromethylbenzothiazoline (33.2 g), m.p. 50° C., is thus obtained.

6-Trifluoromethyl-2-benzothiazolamine can be prepared as described in U.S. Pat. No. 2,832,359.

The present invention also provides pharmaceutical compositions comprising at least one compound of formula (I), or a salt of such a compound, in the pure state or in the form of a composition in which it is combined with a pharmaceutically acceptable and compatible carrier, which can be inert or physiologically active. The pharmaceutical compositions of the invention may be administered orally, parenterally, rectally or topically.

As solid compositions for oral administration, tablets, pills, powders (gelatin capsules, wafer capsules) or granules may be used. In these compositions, the active principle of the invention is mixed with one or more inert diluents such as starch, cellulose, sucrose, lactose or silica.

These compositions can also comprise substances other than diluents, e.g. one or more lubricants such as magnesium stearate or talc, a colouring, a coating (dragees) or a varnish. As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can comprise substances other than diluents, e.g. wetting products, sweeteners, thickeners, flavorings or stabilizers.

The sterile compositions for parenteral administration can preferably be suspensions, emulsions or nonaqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain, apart from the active product, excipients such as cocoa butter, semisynthetic glycerides or polyethylene glycols.

The compositions for topical administration can be, e.g., creams, ointments, lotions, eye washes, mouth washes, nasal drops or aerosols.

In human therapy, the compounds according to the invention are especially useful in the treatment and prevention of convulsive phenomena, schizophrenic disorders, and in particular the deficiency forms of schizophrenia, sleep disorders, phenomena linked to cerebral ischaemia and neurological conditions in which glutamate may be implicated, such as Alzheimer's disease, Huntington's chorea, amyotrophic lateral sclerosis and olivopontocerebellar atrophy.

The doses depend on the effect sought, the treatment period and the administration route used; they are generally between 30 and 300 mg per day in oral administration for an adult, with unit doses ranging from 10 to 100 mg of active substance.

Generally speaking, the doctor will determine the appropriate dosage in accordance with the age and weight and all other factors characteristic of the subject to be treated.

The examples which follow illustrate compositions according to the invention.

EXAMPLE A

Hard gelatin capsules containing 50 mg of active product and having the following composition are prepared according to the usual technique:

| | |
|---|---|
| 3-(2-ethylsulphinylethyl)-2-imino-6-trifluoromethoxybenzothiazoline | 50 mg |
| cellulose | 18 mg |
| lactose | 55 mg |
| colloidal silica | 1 mg |
| carboxymethylstarch sodium | 10 mg |
| talc | 10 mg |
| magnesium stearate | 1 mg |

EXAMPLE B

Tablets containing 50 mg of active product having the following composition are prepared according to the usual technique:

| | |
|---|---|
| 2-imino-3-(2-methylthioethyl)-6-trifluoromethoxybenzothiazoline | 50 mg |
| lactose | 104 mg |
| cellulose | 40 mg |
| polyvidone | 10 mg |
| carboxymethylstarch sodium | 22 mg |
| talc | 10 mg |
| magnesium stearate | 2 mg |
| colloidal silica | 2 mg |
| mixture of hydroxymethylcellulose, glycerol and titanium oxide (72:3.5:24.5) | q.s. 1 finished film-coated tablet weighing 245 mg |

EXAMPLE C

An injectable solution containing 10 mg of active product and having the following composition is prepared:

| | |
|---|---|
| 3-(2-ethylsulphonylethyl)-2-imino-6-trifluoromethoxybenzothiazoline | 10 mg |
| benzoic acid | 80 mg |
| benzyl alcohol | 0.06 cc |
| sodium benzoate | 80 mg |
| ethanol, 95% | 0.4 cc |
| sodium hydroxide | 24 mg |
| propylene glycol | 1.6 cc |
| water | q.s. 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound comprising the formula

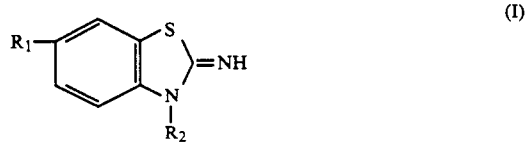

(I)

wherein $R_1$ represents a polyfluoroalkoxy or polyfluoroalkyl, and $R_2$ represents either a residue of formula $-CH_2-(CH(R_4))_n-R_3$, wherein $R_3$ represents dialkylamino, piperidino, 1-pyrrolidinyl, mercapto, acylthio, alkylthio, alkylsulphinyl or alkylsulphonyl, $R_4$ represents hydrogen or alkyl, and n is 0 or 1, or a residue of formula

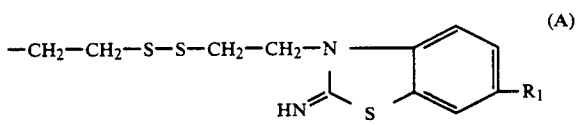

(A)

the aforesaid alkyl radicals and alkyl and alkoxy portions containing 1 to 4 carbon atoms each in a straight or branched chain, and the said acyl portions containing 2 to 4 carbon atoms each, and its enantiomers where it contains an asymmetric centre, and its salts with inorganic or organic acids.

2. A compound according to claim 1, wherein $R_1$ is trifluoromethoxy or trifluoromethyl, $R_4$ is hydrogen, n is 1, and $R_3$ is dimethylamino, piperidino, 1-pyrrolidinyl, mercapto, methylthio, ethylthio, methylsulphinyl, ethylsulphinyl, methylsulphonyl or ethylsulphonyl.

3. A compound according to claim 1, wherein the compound is 3-(2-ethylsulphonylethyl)-2-imino-6-trifluoromethoxybenzothiazoline.

4. A compound according to claim 1, wherein the compound is 2-imino-3-(2-methylsulphinylethyl)-6-trifluoromethoxybenzothiazoline.

5. A pharmaceutical composition which comprises, as active ingredient, a pharmaceutically effective amount of at least one compound as claimed in claim 1, in association with a pharmaceutically acceptable carrier.

6. A method for the treatment of a medical condition associated with the effects of glutamate which comprises administering to a subject in need of such treatment an effective amount of a compound as claimed in claim 1, sufficient to inhibit such effects.

* * * * *